(12) United States Patent
Fu et al.

(10) Patent No.: US 7,749,533 B2
(45) Date of Patent: Jul. 6, 2010

(54) HIGHLY PLASTIC GRANULES FOR MAKING FAST MELTING TABLETS

(75) Inventors: Yourong Fu, West Lafayette, IN (US); Chaul Min Pai, Daejeon (KR); Sang Yeob Park, Daejeon (KR); Gun Seomoon, Daejeon (KR); Kinam Park, West Lafayette, IN (US)

(73) Assignee: Akina, Inc., West Lafayette, IN (US)

( * ) Notice: Subject to any disclaimer, the term of this patent is extended or adjusted under 35 U.S.C. 154(b) by 1397 days.

(21) Appl. No.: 10/841,979

(22) Filed: May 7, 2004

(65) Prior Publication Data

US 2005/0013857 A1 Jan. 20, 2005

Related U.S. Application Data

(60) Provisional application No. 60/468,449, filed on May 7, 2003.

(51) Int. Cl.
*A61K 9/20* (2006.01)
*A61K 9/16* (2006.01)

(52) U.S. Cl. .................. 424/464; 424/465; 424/489

(58) Field of Classification Search .................. None
See application file for complete search history.

(56) References Cited

U.S. PATENT DOCUMENTS

| | | | |
|---|---|---|---|
| 3,885,026 A | 5/1975 | Heinemann et al. |
| 4,371,516 A | 2/1983 | Gregory et al. |
| 5,082,667 A | 1/1992 | Van Scoik |
| 5,178,878 A | 1/1993 | Wehling et al. |
| 5,464,632 A | 11/1995 | Cousin et al. |
| 5,576,014 A | 11/1996 | Mizumoto et al. |
| 5,762,961 A | 6/1998 | Roser et al. |
| 5,939,091 A | 8/1999 | Eoga et al. |
| 5,958,453 A | 9/1999 | Ohno et al. |
| 6,024,981 A | 2/2000 | Khankari et al. |
| 6,048,541 A | 4/2000 | Misra et al. |
| 6,149,938 A | 11/2000 | Bonadeo et al. |
| 6,207,199 B1 | 3/2001 | Allen et al. |
| 6,311,462 B2 | 11/2001 | Amborn et al. |

(Continued)

FOREIGN PATENT DOCUMENTS

WO    WO 95/34293 A1    12/1995

OTHER PUBLICATIONS

D. Parikh, "Handbook of Pharmaceutical Granulation Technology", pp. 60-61, 66-67; (1997).*

(Continued)

*Primary Examiner*—Humera N Sheikh
(74) *Attorney, Agent, or Firm*—James H Meadows; Medicus Associates

(57) ABSTRACT

A fast-melting pharmaceutical tablet comprises a porous, plastic substance, a water penetration enhancer and a binder. One or more drugs can be incorporated into the formulation at different stages of the process so as to afford a pharmaceutically active tablet. Methods of making the pharmaceutical tablet entail combining the porous, plastic material, the water penetration enhancing agent, and the binder so as to form highly plastic granules, which are compressed into tablets. The resulting tablets dissolve rapidly in the mouth and have good hardness with low brittleness. The tablets are particularly valuable to those who have difficulty swallowing conventional pills.

16 Claims, 4 Drawing Sheets

U.S. PATENT DOCUMENTS

| | | | |
|---|---|---|---|
| 6,316,026 | B1 | 11/2001 | Tatara et al. |
| 6,316,029 | B1 | 11/2001 | Jain et al. |
| 6,465,009 | B1 | 10/2002 | Liu et al. |
| 6,465,010 | B1 | 10/2002 | Lagoviyer et al. |
| 6,589,554 | B1 | 7/2003 | Mizumoto et al. |
| 6,596,311 | B1 | 7/2003 | Dobetti |
| 6,717,015 | B2 * | 4/2004 | Keltjens et al. ............ 564/355 |
| 2002/0071857 | A1 | 6/2002 | Kararli |
| 2005/0058705 | A1 | 3/2005 | Remon et al. |

OTHER PUBLICATIONS

Rowe et al., "Handbook of Pharmaceutical Excipients", 4$^{th}$ edition, Pharm. Press. and Am. Pharm. Assn., p. 622; (2003).*

Sastry, S. et al., "Recent technological advances in oral drug delivery—a review", *Pharm. Sci. & Tech. Today* 3: 138-145, 2000.

Seager, H., "Drug-delivery products and Zydis fast-dissolving dosage form," *J. Pharm. Pharmacol.* 50: 375-382, 1998.

Bogner, R., et al., "Fast-dissolving tablets," *U.S. Pharmacist* 27: 34-43, 2002.

Dobetti, L., "Fast-melting tablets: Developments and technologies," *Pharmaceutical Technology North America, Suppl. (Drug Delivery)*, 44-50, 2001.

Chang, R.-K., et al., "Fast-dissolving tablets," *Pharmaceutical Development and Technology*, 24: 52-58, 2000.

Dor, P., et al., "In vitro determination of disintegration time of quick-dissolve tablets using a new method," *Pharma. Devel. & Tech.*, 5: 575-577, 2000.

* cited by examiner

HIGHLY PLASTIC GRANULES FOR MAKING FAST MELTING TABLETS

REFERENCE TO RELATED APPLICATION

This application claims the benefit of U.S. Provisional Application No. 60/468,449, filed May 7, 2003, the disclosure of which is incorporated herein by reference.

BACKGROUND OF THE INVENTION

The term "dysphagia," which refers to a difficulty in swallowing, is common among all age groups. According to one study, people having dysphagia problems make up about 35% of the general population and an additional 30-40% of elderly institutionalized patients as well as 18-22% of all persons in long-term care facilities [see, e.g., Sastry, S. et al., *Pharm. Sci. & Tech. Today* 3: 138-145, 2000]. Common complaints related to difficulty in swallowing tablets are tablet size, surface, form and taste (in the order of frequency of complaints). Geriatric and pediatric patients, as well as traveling patients who may not have ready access to water, prefer dosage forms that can be taken without water and that can be easily swallowed. Another study has shown that an estimated 50% of the population suffers from difficulty in the swallowing of tablets [Seager, H., *J. Pharm. Pharmacol.* 50: 375-382, 1998]. Solid dosage forms that can be disintegrated, dissolved, or suspended by saliva in the mouth resulting in easy swallowing can provide significant benefits to the pediatric and geriatric population, as well as other patients who prefer the convenience of easily swallowable dosage forms.

During the last decade, fast dissolving tablet technologies that make tablets disintegrate in the mouth without additional water intake have drawn a great deal of attention. This novel technology of fast-dissolving tablets is also known as fast-dispersing, rapid-dissolve, rapid-melt and/or quick-disintegrating tablets. A fast-dissolving tablet usually disintegrates into smaller granules which slowly dissolve in the mouth. The disintegration time for fast dissolving tablets varies from a few seconds to more than a minute depending on the formulation and the size of the tablets. The fast dissolving tablets provide patients a convenient alternative to traditional tablets or capsules, which have to be administered with water, and to a liquid dosage form, which is typically bulkier and less accurate in dose. Fast dissolving tablets are particularly needed by the elderly, children, and many others who have difficulty in swallowing.

As used herein, the term "fast-melting tablet" refers to a novel formulation whereby a solid tablet disintegrates into smaller particles resulting in a paste-like structure that can be easily swallowed or dissolved completely in the mouth. Since the terms "fast dissolving tablets" and "fast disintegrating tablets" have been used widely in the literature, they are also used herein to refer to background aspects of the invention and other technologies. As used herein, "FDT" refers to either "fast-dissolving tablet" or "fast-disintegrating tablet."

Processes for Making Fast-Dissolving Tablets

Several technologies have been used previously to produce commercially available FDTs. For example, ZYDIS® (Cardinal Health; Dublin, Ohio), ORASOLV® and DURASOLV® (Cima Labs, Inc.; Eden Prairie, Minn.), and WOWTAB® (Yamanouchi Pharma Technologies, Inc.; Palo Alto, Calif.) technologies have been used to make products in the U.S. market. Although these technologies meet the special requirements for FDTs to some extent, none of them has all the desired properties. For example, to maximize the porous structure of the tablets, current FDT technologies utilize appropriate disintegrating agents and/or highly water-soluble excipients in the tablet formulation. Currently available technologies have been reviewed in the literature [see, e.g., Sastry, S., supra; Seager, H., *J. Pharm. Pharmacol.* 50: 375-382, 1998; and Bogner, R., et al., *U.S. Pharmacist* 27: 34-43, 2002]. The technologies are usually grouped according to the process used in making FDTs, i.e., freeze-drying, molding or compression processes.

Freeze-drying process: Freeze-drying (lyophilization) is a process in which solvent is removed from a frozen drug solution or a frozen drug suspension containing structure-forming excipients. The resulting tablets are usually very light and have porous and plastic structures that allow rapid dissolution. When placed on the tongue the unit dissolves almost instantly to release the incorporated drug. The entire freeze drying process is done at non-elevated temperatures, therefore, eliminating adverse thermal effects that may affect the drug stability during processing. When stored in a dried state, this dosage form has relatively few stability problems during shelf-life. The ZYDIS technology is described in U.S. Pat. No. 4,371,516 (issued to Gregory et al.) and U.S. Pat. No. 5,738,875 (issued to Yarwood et al.). Freeze drying is a relatively expensive manufacturing process and the final dosage forms are very fragile, lacking physical resistance in standard blister packs. Moreover, this approach does not permit accommodating high amounts of active drugs. Additionally, the water soluble drugs may form eutectic mixtures that can not be frozen adequately to form a rigid structure necessary to support itself after solvent is removed, which may cause collapse of the freeze dried cake, and for this reason, the dose for water soluble drugs is usually limited to 60 mg [Seager, H., supra].

Molding process: The major components of molded tablets are typically water-soluble ingredients. The powder mixture is moistened with a solvent (usually water or ethanol), and then the mixture is compressed into mold plates to form a wetted mass (compression molding). The wet mass is molded into tablets under pressures lower than those used in conventional tablet compression. The solvent evaporates by air-drying. Because molded tablets are much less compact than compressed tablets, a higher porous structure is created which enhances dissolution. To improve rapid dissolution, the powder blend usually has to be pushed through a very fine screen. Recently, the molded forms have also been prepared directly from a molten matrix in which the drug is dissolved or dispersed (heat molding) or by evaporating the solvent from a drug solution or suspension at ambient pressure (no-vacuum lyophilization) [Dobetti, L., *Pharmaceutical Technology North America, Suppl.* (*Drug Delivery*), 44-50, 2001]. Because the major component in the dispersion matrix is generally made from water-soluble sugars, molded tablets disintegrate more rapidly and offer improved taste. Unfortunately, molded tablets typically do not have great mechanical strength. See, e.g., U.S. Pat. No. 5,082,667 (issued to Van Scoik). The chances of erosion and breakage of the molded tablets during tablet handling and opening blister pockets are high. By using nonconventional equipment and/or multistep processes, FDTs with both adequate mechanical strength and good disintegration have been prepared by molding techniques. Using a nonconventional approach, however, requires more investment in machinery. As compared with FDTs prepared by freeze-drying, molded tablets can be produced more simply and efficiently on an industrial scale, although disintegration times are not comparable to those of lyophilized forms.

Compression process: Using a conventional tablet press for making fast dissolving tablets is very attractive because of low manufacturing cost and ease in technology transfer. However, a tablet press has been designed to make conventional tablets. When making conventional tablets, maintaining high tablet porosity is not a primary concern. High compression force is used to ensure the tablet strength. Many strategies have been tried to achieve high porosity and adequate tablet strength using the tablet press. The compression process is most widely used for making FDTs. The three widely used approaches are: granulation methods, special excipients methods, and compaction and subsequent treatment methods. Because the present invention is related to the compression method, the aforementioned approaches are described below in detail.

Granulation methods: Wet granulation, dry granulation, spray drying, and flash heating methods are all distinct methods used to obtain granules for making FDTs. These methods are briefly discussed hereinbelow.

a. Wet Granulation

U.S. Pat. No. 6,149,938 (issued to Bonadeo et al.) proposes a process of producing rapidly disintegrable, mouth-soluble tablets by wet granulation in a fluidized bed. The inventors claim that even with effervescent agents presented in the tablet with lower than 5%, similar quick disintegration times can be achieved. Furthermore, they found that fast disintegration times can be achieved using only the acid component of the effervescent couple. They suggest use of polyalcohols (e.g., mannitol, xylitol, sorbitol, maltitol, erythritol and lactitol), 1-30% of an edible acid, and an active ingredient as the dry mixture. This mixture was wet granulated with an aqueous solution of a water-soluble or water-dispersible polymer (e.g., poly(ethylene glycols), carrageenan, and ethylcellulose) which consists 1-10% of the final weight of the granule in a fluid bed. Granules with high porosity and low apparent density were obtained, and the tablets made by such granules are reported to have rapidly disintegration time ranging from 3 to 30 sec in the saliva.

U.S. Pat. No. 6,316,029 (issued to Jain et al.) proposes a rapidly disintegrating tablet for a poorly soluble active ingredient. First, nanoparticles were formed by mechanical grinding, precipitation, or any other suitable size reduction process. Those nanoparticles, less than 2,000 nm, were attached to the surface stabilizer, such as nonionic and ionic surfactants. The particles were granulated with at least one pharmaceutically acceptable water-soluble or water-dispersible excipient using a fluid bed; the granules were made into tablets. The tablets had complete disintegration or dissolution in less than 3 min.

b. Dry Granulation

U.S. Pat. No. 5,939,091 (issued to Eoga et al.) proposes a method of making FDTs by dry granulation. Higher density alkali earth metal salts and water soluble carbohydrates do not provide quick disintegration and a smooth mouth feel. Low density alkali earth metal salts and water soluble carbohydrates are difficult to compress and may cause inadequate content uniformity. Thus, low density alkali earth metal salts or water soluble carbohydrates were pre-compacted, and the resulting granules were compressed into tablets that could dissolve fast. In this process, a powdered material with a density of 0.2-0.55 g/ml was pre-compacted to increase the density to 0.4-0.75 g/ml by applying a force speed ranging from about 1.0 kN/cm to about 9.0 kN/cm. The resulting granules were compressed into tablets.

c. Spray Drying

Spray-drying provides a fast and economical way of removing solvents and producing porous and plastic, fine powders. U.S. Pat. No. 6,207,199 (issued to Allen et al.) proposes a particulate support matrix for use in forming fast-dissolving tablets by using a spray-drying technique. The components in this particulate support matrix include supporting agents composed of two polypeptide components of the same net charge (preferably non-hydrolyzed gelatin and hydrolyzed gelatin), a bulking agent (mannitol), and a volatilizing agent. The mixtures of above components were spray dried to obtain porous granules. By incorporating a volatilizing agent (in most cases, ethanol), the surface tension of the droplets was further reduced during spray-drying and more pores and channels were created. The solubility of the matrix was further increased (in a matter of seconds) when combined with a bulking agent. A minimal amount of effervescent agents may be optionally included to further accelerate the dissolution rate. To aid in keeping the tablets intact during handling, a thin coating of polymeric material may also be applied externally. Active ingredients can be micro-encapsulated or nano-encapsulated to further achieve taste-masking.

d. Flash Heat Process

Fuisz et al. have introduced the shearform technologies to make FDTs. This technology, as described in PCT Publication WO 95/34293 and U.S. Pat. No. 6,048,541 utilizes a unique spinning mechanism to produce a floss-like crystalline structure, much like cotton candy. In this process, the feedstock is subjected to centrifugal force and to a temperature gradient simultaneously. An internal flow is created by this condition to force the flowing mass out of the opening provided in the perimeter of a spinning head. The mass is cooled down as it comes out of the opening to form a discrete fiber structure, as seen in cotton candy. The speed of spinning is about 3,000-4,000 rpm and the temperature gradient is about 180-250° C. The carrier materials include saccharides, polysaccharides, and mixtures thereof. The produced floss needs to be recrystallized to form freely flowing granules with self-binding properties.

Specific excipients methods: These methods focus on selecting specific excipients, such as water-insoluble calcium salt, specific disintegrant combination, and specific sugar combination, as the main component for FDTs.

a. Calcium Salt as the Specific Excipient

U.S. Pat. No. 6,596,311 (issued to Dobetti) proposes a formulation using insoluble inorganic excipients as the main component for fast disintegration tablets. According to this reference, disintegration of a tablet in the oral cavity depends on the quantity of the disintegrant and insoluble inorganic excipient used. The disintegration also depends on the relative weight ratio between the water insoluble and soluble excipients, if the water soluble excipients are used. It was also found that in their formulation, sufficient compression could be applied to form tablets with strong tensile strength and low friability. The disintegration rates reportedly were not significantly affected by the high compression force. Substantially water insoluble components include water-insoluble excipients, water-insoluble drugs (either coated or uncoated), and water-insoluble lubricant and glidant. The water-insoluble excipients include insoluble inorganic salt (e.g., di- or tribasic calcium phosphate) or organic filler (e.g., microcrystalline cellulose).

b. Sugar Based Excipients

Sugar-based excipients, such as sorbitol, mannitol, dextrose, xylitol, fructose, maltose, isomalt, maltitol, lactitol, starch hydrolysate, and polydextrose, have been widely used as bulking agents because of their high aqueous solubility and sweetness, pleasing mouth-feel and good taste masking. Nearly all formulations for rapidly dissolving tablets incorporate some sugar materials in their formulations [Chang, R.-K., et al., Pharmaceutical Technology, 24: 52-58, 2000].

A further proposal is described in U.S. Pat. No. 5,576,014 (issued to Mizumoto et al.), U.S. Pat. No. 6,589,554 (issued to Mizumoto et al.) and U.S. Pat. No. 6,465,009 (issued to Liu et al.), which related to the so-called WOWTAB® technology of Yamanouchi Pharmaceutical Co. This technology employs a combination of low and high moldability saccharides to produce fast dissolving tablets using conventional granulation and tableting techniques. As set forth in these references, saccharides are divided into two groups: saccharides with high moldability and low moldability. The saccharides having "low moldability" are those producing tablets with a hardness between 0-2 kg when 150 mg of such a saccharide is compressed under pressure of 10-50 kg/cm$^2$ using a die of 8 mm in diameter. Exemplary low moldability saccharides include lactose, mannitol, glucose, sucrose, and xylitol. The saccharides having "high moldability" are those producing tablets with hardness above 2 kg when prepared under identical conditions. Typical high moldability saccharides consist of maltose, maltitol, sorbitol and oligosaccharides. When tablets are made by compressing a saccharide having low moldability or a saccharide having high moldability alone, the desired properties of adequate hardness and quick disintegration in the mouth reportedly cannot be achieved simultaneously. Moreover, if a saccharide having low moldability and a saccharide having high moldability are mixed (physical mixture) before tableting, quick disintegration and dissolution in the mouth cannot be obtained. According to these references, no single saccharide can make tablets having both high strength and fast disintegration properties. For this reason, a saccharide having low moldability was granulated with a saccharide having high moldability as a binder. The low moldability saccharides were used as the main component. The blending ratio of a high moldability saccharide to the low moldability saccharide ranged from 2 to 20% by weight, preferably from 5 to 10% by weight. Up to 50% (w/w) of the tablet weight can be the active ingredient in these systems. Tablets made by compression of these granules are claimed to show an adequate hardness and fast disintegration and dissolution when put in the mouth.

c. Disintegrants

Most fast dissolving tablet formulations use some type of disintegrant. Some formulations use effervescent couples as their disintegrant, while others use a combination of disintegrants. A summary of different types of non-effervescent disintegrants used in the pharmaceutical area is given by Dobetti (U.S. Pat. No. 6,596,311).

As disclosed by U.S. Pat. No. 5,464,632 (issued to Cousin et al.), the FLASHTAB® technology of Laboratoires Prographarm (France) produces tablets by compression of granular excipients. Excipients used in this technology comprise two groups of components. One group is disintegrating agents, such as carboxymethylcellulose or insoluble reticulated polyvinylpyrrolidone. The other group is swelling agents, such as carboxymethylcellulose, starch, modified starch, carboxymethylated starch, microcrystalline cellulose, and possibly directly compressible sugars. The mixture of excipients was prepared by either dry or wet granulation methods. The produced tablets are known to have satisfactory physical resistance and disintegrate in the mouth within 1 min.

U.S. Pat. No. 5,178,878 (issued to Wehling et al.), proposes the ORASOLV® technology of Cima Labs, Inc. This references discloses a low pressure compression method of making fast dissolving tablets that uses an effervescent disintegration agent. Effervescent disintegration agents are compounds that release gas as they contact water. The most widely used effervescent disintegration pairs usually include an acid source and a carbonate source. The acid source includes citric acid, tartaric acid, malic acid, fumaric acid, adipic acid, and succinic acids. The carbonate source includes sodium bicarbonate, sodium carbonate, potassium bicarbonate and potassium carbonate. The carbon dioxide evolved from the reaction may provide patients some "fizzing" sensation, which is a "positive" organoleptic sensation. Formulations described in the patent include an effervescent disintegration agent, a pharmaceutical ingredient in a microparticle form, and other excipients such as binders and non-effervescent disintegrants. The amount of an effervescent disintegration agent is in general about 20-25% of the total weight of the tablet. A pharmaceutical ingredient incorporated in the tablet is in a microparticle form. The microparticles may be prepared as a microcapsule or as a matrix-type microparticle. The microparticle form can also be used to cover the bad taste of drugs as well as to control the drug release profiles. Because of the soft and fragile nature of ORASOLV® tablets, a special packaging system, referred to as PAKSOLVE and disclosed in U.S. Pat. No. 6,311,462 (issued to Amborn et al.), was developed to protect the tablets from breaking during transport and storage. Also, DURASOLV® technology was developed by the same company to provide stronger tablets for packaging in foil pouches or bottles, as described in U.S. Pat. No. 6,024,981 (issued to Khankari et al.). The key ingredients in this formulation are a non-direct compression filler and a lubricant. A very fine filler, known as a non-direct compression filler, is used as the main ingredient. The materials that can be used as non-direct compression filler are non-direct compression sugars and sugar alcohols, such as dextrose, mannitol, sorbitol, lactose and sucrose. The amount of a non-direct compression filler is usually about 60-95% of the total tablet weight.

Compaction and subsequent treatments: These methods produce tablets compressed at low pressure first and then apply various after-treatments, such as sublimation, sintering, and humidity treatments, to make soft tablets strong.

a. Sublimation

In sublimation technologies, the high porosity necessary for fast disintegration is achieved by using volatile materials. Inert solid ingredients, such as urea, ammonium carbonate, ammonium bicarbonate, hexamethylene tetramine, and camphor, can volatilize readily. When these volatile materials are compressed into tablets, they can be removed via sublimation, which generates porous structures. U.S. Pat. No. 3,855,026 (issued to Heinemann et al.) discloses a process to prepare porous tablets by sublimation. The mixtures of volatile adjuvants were made into tablets which were subsequently heated to remove the adjuvants, because a residual amount of the adjuvants in the tablet may have deleterious effects on the patients. Another method is proposed by U.S. Pat. No. 5,762,961 (issued to Roser et al.), which discloses a method to produce rapidly soluble tablets by sublimation. The components in the formulation include a volatile salt (such as ammonium bicarbonate, ammonium acetate and ammonium carbonate) in the amount of 30-50% (w/w) of the tablet, a diluent (e.g., trehalose or lactose), a binder, and other adjuvants.

b. Humidity Treatment

It is known that certain sugars change from amorphous state to crystalline state when their solution is spray-dried or used as a binder solution. Further investigations have shown that when an amorphous sugar is treated to go through the humidification and drying process, it changes to a crystalline state. This change increases the tablet strength substantially.

U.S. Pat. No. 6,589,554 (Mizumoto et al.), mentioned hereinabove, proposes humidification and drying of a drug, a sugar, and an amorphous sugar capable of transforming from amorphous to the crystalline state. The major function of the sugar is to dissolve inside the buccal cavity. The amount of the sugar in the formulation can be adjusted according to the drug content and tablet size. Preferred sugars include lactose, glucose, trehalose, mannitol, erythritol, and the like. The "amorphous sugars" are those that can form an amorphous state by spray drying, freeze-drying, or other granulation methods. The "amorphous sugars" include glucose, lactose, maltose, sorbitol, trehalose, lactitol, fructose, and the like. The crystalline form of the sugars dissolved in solvent is sprayed against the drug. The humidification and subsequent drying process is used to increase the tablet strength. The relative humidity is determined by the apparent critical relative humidity of the mixture of a drug, and an amorphous sugar. A relative humidity greater than or equal to the critical relative humidity of this mixture is chosen for the humid condition. The advantage of using amorphous sugars is that they have low critical relative humidity, so that they can absorb water even at low moisture levels. The crystalline form of the sugars has difficulty in controlling moisture absorption. Moisture absorption of the crystalline form is not sufficient enough to strengthen the tablets at a low humidity condition. If a high humidity condition is used, tablets may adhere together causing manufacturing problems. Another advantage of using amorphous sugars is that transformation of the amorphous state to the crystalline state is irreversible. The sugars in the crystalline state have a high critical moisture point. The strengthened tablets are less susceptible to moisture.

U.S. Pat. No. 6,465,009 (Liu et al.), mentioned hereinabove, discloses a system for making fast dissolving tablets by humidity treatment. Water soluble polymers are used as a binder solution. The process includes the following steps: a water soluble polymer was used as a binder solution to granulate active ingredients and other excipients, such as low modability sugars (e.g., mannitol, lactose, glucose, sucrose, and lactitol); the granules were then compressed into tablets; the tablets were humidified at relative humidity of about 50-100%; and the tablets were dried. Reportedly, the hardness of the tablet is about 0.5-12.0 kilopounds and the in vivo disintegration time is about 1 sec to 40 sec.

As disclosed in U.S. Pat. No. 6,316,026 (issued to Tatara et al.), fast dissolving tablets can be made by moisture treatment and an apparatus to handle the fragile tablets before moisture treatment. An active ingredient and one or more water-soluble saccharides were compressed at pressure between 0.01 and 0.2 ton/cm$^2$. The tablet was then moisturized and dried to produce a porosity between 20 and 40%. The active ingredient in the formulation should be preferably less than 30%. The useful saccharides in the formulation include erythritol, xylitol and mannitol. The tablet manufacturing apparatus includes a rotary punch-press, a relay conveyor for transferring tablets, a moisturizing section, a drying section and a delivery conveyor. In the moisturizing section, the condition was set to allow tablets moisturized at 45° C., 95% relative humidity for 60 sec. In the drying section, the temperature was set to 50° C. for 60 sec. By using this apparatus the fragile tablets before moisture treatment were gently transferred throughout the process.

c. Sintering

A further method is disclosed by U.S. Pat. No. 6,465,010 (issued to Lagoviyer et al.), which describes a process that increases tablet strength by sintering the tablet components at high temperatures and resolidifying after the temperature decreases subsequently. The components in this formulation include bulk agents, structure agents, solvent, and binding agents. A bulk agent in this formulation is to provide bulk volume to the overall tablet and its content ranges from approximately 10% to 95% of the whole tablet. Suitable bulking agents include carbohydrates (e.g., sucrose, mannitol, and sorbitol), calcium carbonate, magnesium carbonate, and the like. The suitable structure agents should provide a porous support structure allowing quick dissolution of the tablets in the mouth. The structural agents include agar, gelatin, albumen, and chondroitin. The preferred structural agent was gelatin. The amount of gelatin ranged from approximately 1 to 3%. Choice of solvent to dissolve the mixture of bulking agent/structural agent is based on the ability to provide a desired porosity to the bead or granulated product upon drying. Solvents can be chosen from water, ethyl alcohol, isopropyl alcohol, or a mixture thereof. The preferred solvent is the mixture of ethyl alcohol and water in a ratio ranging from 1:1 to 1:100. The binders need to melt at the sintering stage, and form bonding among granules and resolidify as the temperature of the final sintering or heating step decreases. Binders are water soluble polymers and the preferred binding agent is poly(ethylene glycol) (PEG) with a molecular weight of approximately 1,000 to 1,000,000. PEG melts at about 50 to 90° C. PEG has the advantage of functioning both as a binder and as a capillary attractant. The amount of binding polymer ranged from 0.5% to 25% of the weight of the final product.

SUMMARY OF THE INVENTION

The present invention is directed to a pharmaceutical tablet capable of melting rapidly in the buccal cavity. The tablet comprises a plurality of highly plastic granules, wherein the granules comprise a porous, plastic substance, a water penetration enhancer, and a binder. The tablet can be a placebo, in which case it lacks an active pharmaceutical ingredient. On the other hand, it will more usually comprise a drug.

A porous, plastic substance for use in the invention is conveniently characterized and/or selected by exhibiting plastic deformation when 500 mg of the substance is compressed in a 0.5-inch diameter die at a pressure less than about 1,500 pounds. The porous, plastic substance typically comprises from about 1% to about 95% of the tablet by weight.

A water penetration enhancer of the invention is conveniently characterized and/or selected by conducting the following test: First, a 200 mg tablet of the material is formed at 300 pounds in a 0.5 inch diameter die. Then, the tablet is placed on top of a 0.5 ml water drop that is provided on a flat surface on which the water drop does not spread, i.e., the surface is not wetted. If the enhancer tablet absorbs the water and exhibits complete wetting within 60 seconds, as evidenced by the appearance of water on its upper surface, the material is suitable as a water penetration enhancer for use in the present invention. Typically, the water penetration enhancer comprises from about 1% to about 95% of the tablet by weight.

A binder of the present invention is a conventional one that has been selected to permit particles of the porous, plastic substance and the water penetration enhancer to adhere to each other sufficiently to prevent particle segregation and to increase granule adherence at the low pressure used to form the tablet. The binder typically comprises from about 1% to about 90% of the tablet by weight.

In one embodiment of the invention, the porous, plastic substance and the water penetration enhancer can be the same material, i.e., both functions of providing a material having suitable porosity and providing one having suitable water penetration properties can be imparted to the tablet by the same substance. An example in this regard is fructose.

A tablet of the present invention generally has a total tablet weight in the range of about 5 mg to about 5,000 mg, preferably in the range of 50 mg to 500 mg. A tablet of the invention also is characterized by melting in the mouth in less than about 90 seconds, preferably in less than about 60 seconds. In addition to the ingredients mentioned above, a tablet may also comprise at least one additional ingredient, e.g., a surfactant, superdisintegrant, superporous hydrogel particle, effervescent agent, lubricant, flavoring agent, and/or coloring agent.

A method for making a fast-melting pharmaceutical tablet of the present invention comprises combining a porous, plastic substance, and a water penetration enhancer to form an admixture thereof; treating the admixture with an amount of a binder effective to form a mass of agglomerated particles thereof; sieving and/or drying the agglomerated particles so as to isolate a plurality of highly plastic granules; and compressing the highly plastic granules under low pressure to afford the fast melting pharmaceutical tablet. Such method preferably also comprises intimately combining an active pharmaceutical ingredient with the porous, plastic substance, the water penetration enhancer, and/or the binder prior to admixing the porous, plastic substance and the water penetration enhancer. The tablet compression pressure used to compress the highly plastic granules into tablets is generally less than about 150 MPa, preferably less than about 35 MPa, and more preferably less than about 10 MPa. A pharmaceutical tablet having fast dissolving properties made by such method is contemplated.

DETAILED DESCRIPTION OF THE INVENTION

The three main properties required of fast melting tablets are (i) high porosity of a tablet for water absorption, (ii) penetration of water into the tablet core within seconds, and (iii) high mechanical strength of a tablet for easy handling. These three tablet properties are achieved simultaneously according to the principles of the present invention by combining chemical components that afford the aforementioned properties. Thus, a pharmaceutical tablet of the invention comprises three classes of components: (i) a porous and plastic material (Component 1); (ii) a water penetration enhancer (Component 2); and (iii) a binder (Component 3). When these three primary components are combined and processed as described herein, highly plastic granules can be obtained. The highly plastic granules can then be compressed at low pressure to form a fast melting pharmaceutical tablet.

As used herein, the term "highly plastic granules" refers to those granules compressed into a fast melting tablet according to the principles of the present invention. In particular, such granules are "highly plastic" whenever 500 mg of the granules, compressed into a 0.5-inch diameter die at a pressure less than 1,500 pounds, exhibit a hardness of the formed tablet greater than about 7 Newton (N) or a friability of the formed tablet less than about 5%. Tablets produced by compressing such highly plastic granules at low pressures exhibit high porosity and exceptionally low friability. When such a tablet prepared with the highly plastic granules is placed into the buccal cavity, and particularly on the tongue, it melts very fast.

As used herein, the term "melting" refers to loss of tablet shape by either disintegration or partial dissolution into a paste-like structure for easy swallowing. The melting time depends on the size and dimension of a fast-melting tablet, but in general the smaller the tablet, the faster is the melting. The melting time ranges from less than several seconds for small size tablets to more than 60 seconds for larger tablets.

To any of the aforementioned three components can be added surfactants, superdisintegrants, superporous hydrogel particles, effervescent agents, lubricants, flavoring agents, or coloring agents to improve tablet performances and/or manufacturing processes. Alternatively, any of these other ingredients can be added to the tablet formulation after formation of the highly plastic granules and before compression into tablets.

Figure 1:
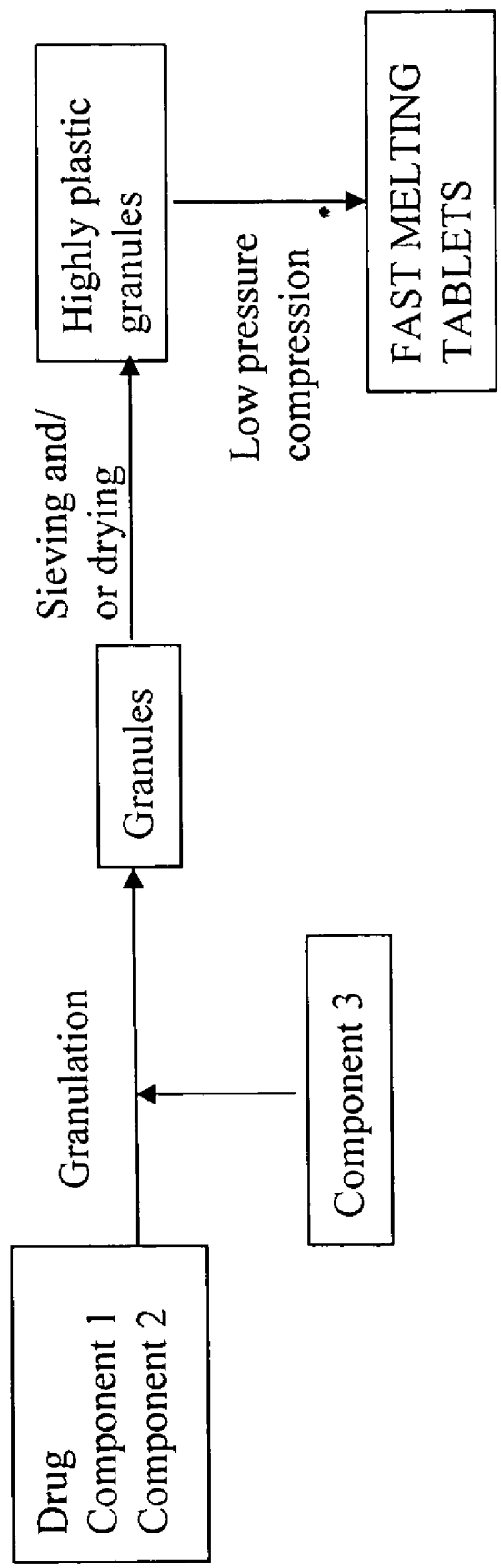
FIG. 1 is a schematic representation of general processing steps for making highly plastic granules and fast-melting tablets.

FIG. 1 illustrates a typical process for making highly plastic granules and fast-melting tablets according to the present invention. In the process depicted in FIG. 1, a drug is mixed with Component 1 and Component 2 before granulation takes place. The drug does not have to be mixed with Components 1 and 2 before granulation, however, as is discussed more fully hereinbelow. Moreover, Component 1 and Component 2 can be the same chemical compound.

Figure 2:
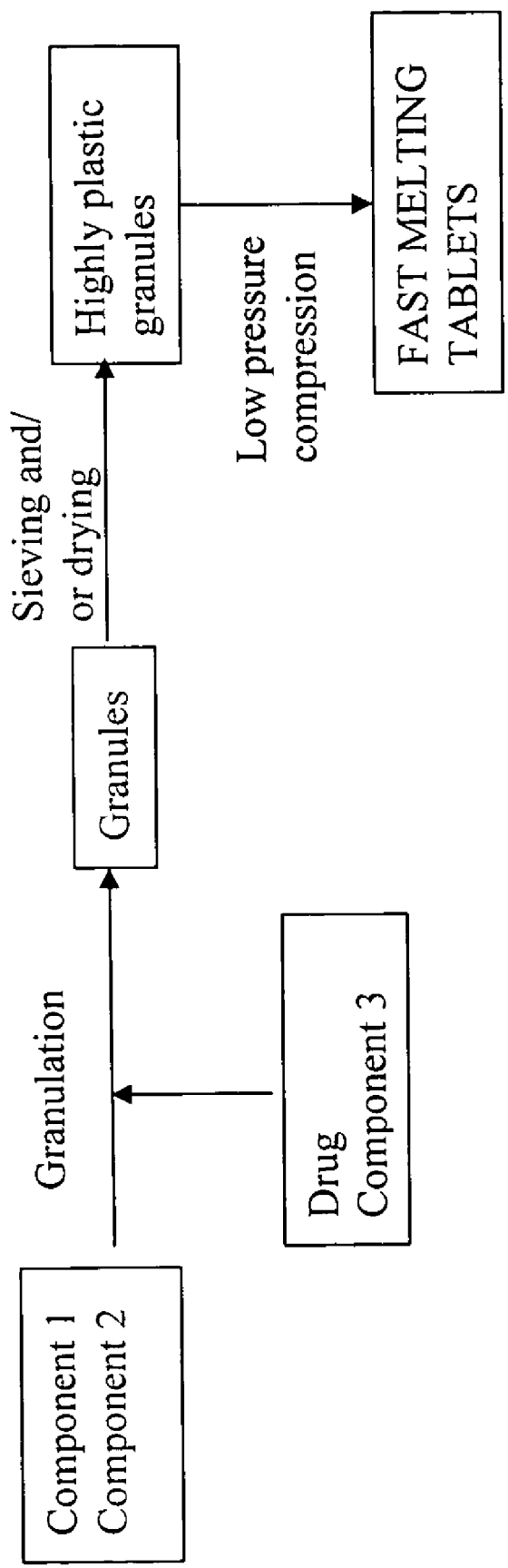
FIG. 2 shows an alternative processing method where a drug is added to Component 3 (as described in Example 13) for making highly plastic granules and fast-melting tablets.

In another embodiment, shown in FIG. 2, the drug is added to Component 3. This procedure is useful, for example, for drugs that have very low dose or that are already in the solution state.

Figure 3:
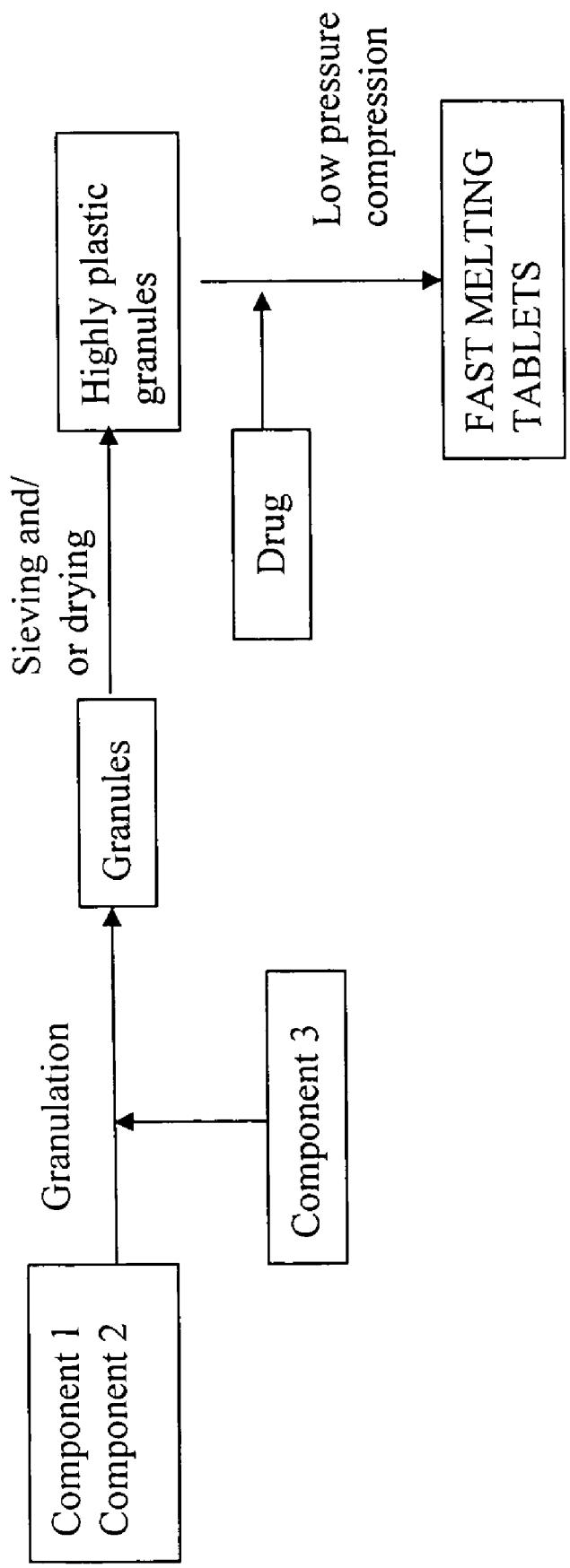
FIG. 3 depicts an alternative process where a drug is added to highly plastic granules (as described in Example 14) for making highly plastic granules and fast-melting tablets.

In another embodiment of the invention, as shown in FIG. 3, highly plastic granules without the drug can be prepared first, and then the drug can be mixed in later. This procedure is especially useful if the drug is sensitive to the solvents used for granulation.

Figure 4:
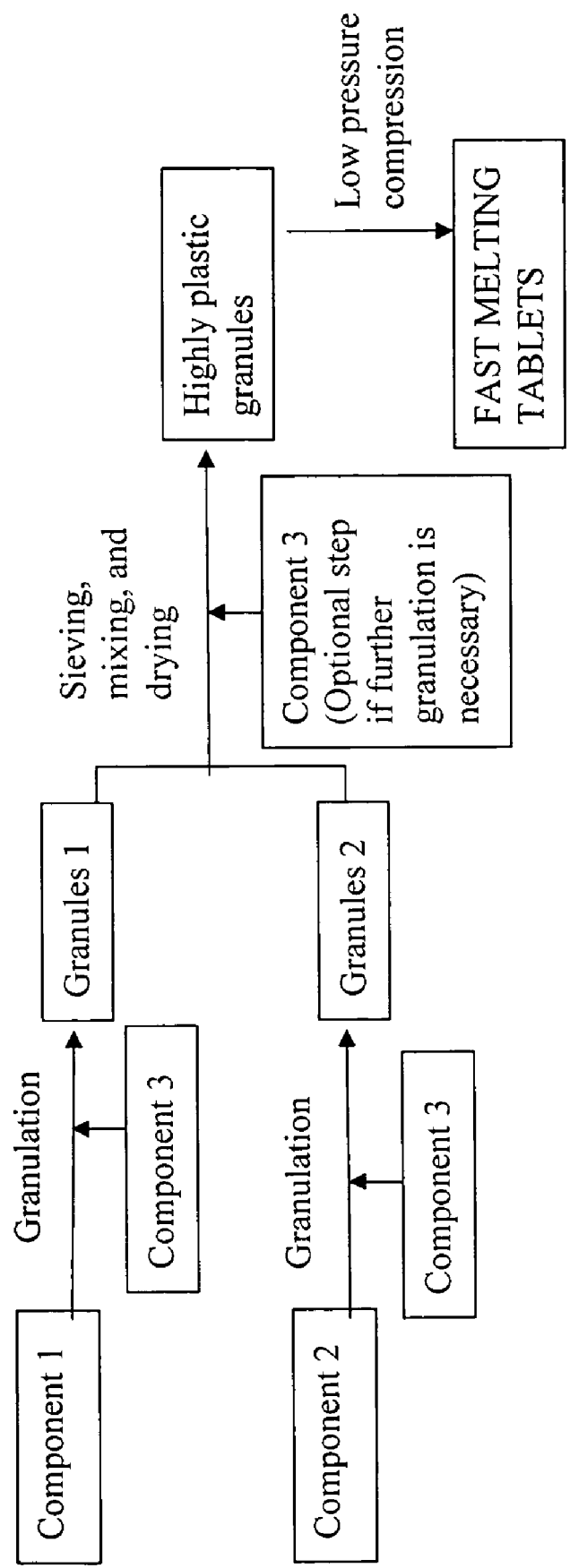
FIG. 4 illustrates another tablet forming process where Component 1 and Component 2 can be granulated separately and then combined later to form highly plastic granules. Granules of Component 1 and Component 2 can be further granulated with the help of Component 3. Drug can be added in any step before the low pressure compression step.

Additionally, as shown in FIG. 4, Components 1 and 2 do not have to be granulated at the same time. Component 1 can be granulated independently from Component 2 to make two different types of agglomerated particles (granules). The granules of Component 1 and Component 2 can be mixed together along with other components. Granules comprising Component 1 and Component 2 can be further granulated with Component 3. One or more drugs can be added in any step before the low compression step takes place.

As is evident from the above, a number of variations in process steps can afford fast melting tablets having similar properties.

Rationale for the Three-Component System

Component 1 of the present invention is chosen from porous and plastic excipients that are pharmaceutically acceptable. The porous, plastic material is water soluble or water dispersible, sometimes almost instantaneously upon contact with water. Suitable powders with porous structure and plastic property are those that can be made into a tablet when 500 mg of such powders are pressed using a 0.5-inch diameter die at a pressure less than 1,500 pounds, whereby the formed tablet maintains its shape and size, i.e., exhibits plastic properties. Plastic deformation of powders dramatically increases the chance of inter-particle contacts necessary for forming bonds between particles.

If a porous and plastic material of the invention is polymeric, it is essential to prevent formation of a viscous layer of the material at the tablet surface when it dissolves in aqueous medium. One way of making such tablets is to mix the porous and plastic materials (Component 1) with a water penetration enhancer (Component 2) at certain ratios and compress them at low pressure resulting in plastic deformation of porous and plastic materials to create intimate contacts among particles. In this process, the porous and plastic particles are separated by water penetration enhancing particles (Component 2), which prevent formation of a viscous layer on the tablet surface. In the present invention, Component 1 and Component 2 are often different substances, but in some cases they can be the same material.

Although the porous and plastic materials can make close contacts to increase the chance of bonding by compression, formation of really strong bonding among granules at the pressure mentioned above requires a suitable binder (Component 3). The binder here can also secure the porous material and water penetration enhancer during granulation. Without the binder those two components can be easily segregated during mixing. The binder can be a liquid or semi-solid, such as a binder in paste form. If the binder is in the liquid or semi-solid state, it should not significantly destroy the porous structure of the porous materials. One way of achieving this is to use high concentrations of the binder to lower the water activity. Another way of achieving this is to allow only a short contact time for the porous structure not to be destroyed by the binder solution when making granules using relatively low concentrations of the binder. For example, the solvent can be instantly dried after wetting in a fluidized bed granulator, so that the porous structure can be maintained even though a relatively low concentration of the binder is used.

Components of Fast Melting Tablets Based on Highly Plastic Granules

Component 1: Porous and Plastic Materials

The term "porous, plastic material", and equivalents thereof, as used herein, refers to any material that is (i) porous, with a porosity (as defined by the pore volume divided by the total volume) higher than about 0.14 or a density (as defined by the weight divided by the volume) lower than about 0.86, and (ii) undergoes plastic deformation (i.e., the formed tablet maintains its shape and size) when 500 mg of such powders are pressed using a 0.5-inch diameter die at a pressure less than 1,500 pounds. Generally, if the compression force is higher than 1,500 pounds, then the formed tablets usually do not maintain the fast melting property.

A porous and plastic material is preferably water soluble. A porous and plastic material with high water solubility can occupy from 1% to 95% of a whole tablet by weight. If the concentration of Component 1 is less than about 1%, it cannot provide enough contacts with other components to increase the chance of binding by compression. If the concentration of Component 1 is higher than about 95%, then other components, such as Component 2, Component 3, drug, lubricant, etc., cannot be included.

A porous and plastic material of the invention can be either purchased commercially or can be made by various methods, e.g., spray drying, granulation with fluidized bed granulator, and so forth. Examples of a porous and plastic material that can be used in making highly plastic granules include, but are not limited to, saccharides, including fructose, lactitol, lactose, maltitol, maltose, mannitol, sorbitol, sucrose, erythritol, and xylitol, as well as organic polymers, such as maltodextrin, dextrin, ethylcellulose, polymethacrylates, and pregelatinated starch (e.g., LYCATAB® by Roquette American Inc.). Maltodextrin can be obtained commercially, and examples are MALTRIN series (maltodextrins and corn syrup solids forms by Grain Processing Corp.), MALTRIN QD series (maltodextrins and corn syrup solids quick-dispersing forms by Grain Processing Corp.), and GLUCIDEX® IT (maltodextrins and spray-dried glucose syrups by Roquette American Inc.). Maltrin QD series and ADVANTOSE FS 95 Fructose, or combinations thereof, are preferred because they are made to have high porosity inside agglomerates in addition to their excellent binding property.

Other materials that can form suitable porous and plastic structures include gum arabic, xanthan gum and its derivatives, guar gum and its derivatives, seaweed gums, carrageenan, dextran, gelatin, alginates, pectins, starch and starch derivatives (e.g., hydroxypropyl starch or carboxymethyl starch), cellulose esters (e.g., carboxymethylcellulose or cellulose ethers hydroxyethyl-methylcelluloses), homo- or co-polymers of an unsaturated acid (e.g., acrylic acid or a salt thereof), homo- or co-polymers of an unsaturated amide (e.g., acrylamide), homo- or co-polymers of ethylene imine, a vinyl polymer (e.g., poly(vinyl alcohol)), homo- or co-polymers of a vinyl ester (e.g., vinylpyrrolidone, vinyloxazolidone, vinylmethyloxazolidone, vinylamine, and vinylpyrridine), alkylglycol, and polyalkylene oxide (e.g., polyethylene oxide) and oxyethylene alkylether, dextrates, dextrin, dextrose, microcrystalline cellulose, silicified microcrystalline cellulose, powdered cellulose, cellulose acetate, calcium sulfate, calcium carbonate, dibasic calcium phosphate, tribasic calcium phosphate, and carboxymethylcellulose-calcium salt.

Component 2: Water Penetration Enhancers

A water penetration enhancer of the invention is used to make a tablet disintegrate fast. As used herein, a "water penetration enhancer" is defined phenomenologically as follows: For a 200 mg of a candidate penetration enhancement material is compressed at 300 pounds in a 0.5-inch diameter die, the tablet formed should be completely wetted within 60 seconds when it is placed on top of a 0.5 ml water drop placed on a flat surface that is not wetted, i.e., the water drop does not spread on the surface. Complete wetting is evidenced by appearance of water on the top of the tablet within the 60 second time frame.

For use in making fast-melting tablets, a water penetration enhancer should be highly water-soluble, or it should at least be highly dispersible. A water penetration enhancer can occupy from 10% to 95% of a whole tablet by weight. Typically, if the concentration of Component 2 is less than about 10%, it cannot effectively provide water penetration enhancing effect. If the concentration of Component 2 is higher than about 95%, then other components, such as Component 1, Component 3, drug, lubricant, etc., cannot be included.

Common water penetration enhancers are highly water-soluble carbohydrates, which are often used as diluents. Any types of carbohydrates can be used in the formulations described in this invention. Examples are dextrates, dextrin, dextrose, fructose, lactitol, lactose, maltitol, maltose, mannitol, sorbitol, sucrose, erythritol, and xylitol. Those diluents that are less water-soluble but highly dispersible include microcrystalline cellulose, silicified microcrystalline cellulose, powdered cellulose, cellulose acetate, calcium sulfate, calcium carbonate, dibasic calcium phosphate, tribasic calcium phosphate, and carboxymethylcellulose-calcium salt. Various combinations of carbohydrates and polymers can also be used. Examples are STARLAC® (spray-dried solid containing 15% maize starch and 85% alpha-lactose monohydrate from Roquette American, Inc.), MICROCELAC® (spray-dried solid containing 75% alpha-lactose monohydrate and 25% microcrystalline cellulose from Meggle excipients & technology), and CELLACTOSE® (spray-dried compound consisting of 75% alpha-lactose monohydrate and 25% cellulose powder by Meggle excipients & technology). The preferred grade of the material used as water penetration enhancers, or bulk diluents, is the direct compression grade. The materials prepared to have high porosity, e.g., by spray drying, are even more preferred. Examples of porous water penetration enhancers, or bulk diluents, are STARLAC®, MICROCELAC®, CELLACTOSE®, MANNOGEM EZ Spray® (spray-dried mannitol from SPI Pharma. Inc.).

Component 3: Binders

In the present invention, the primary function of a binder is to make bonds between Component 1 and Component 2, thereby preventing the two components from segregating, and to increase the bonding efficiency among granules at low compression pressure used in making tablets. The binder can be in liquid or semi-solid form, depending on the method of granulation. One requirement for the binder is that the binder in a solution or semi-solid form should not significantly destroy the porous structure of a material by dissolving it. Accordingly, it is important to maintain the porous structure of Components 1 and 2 as much as possible. This can be done, for example, by simply lowering the water activity using high concentrations of a binder. A simple test can be performed to examine the suitability of a binder as follows: 1 mL of a binder is added to 0.5 g of the porous and plastic material; if the porous materials are not totally dissolved within 10 sec, the binder is a potential candidate that can be used for making the fast melting tablets according to the principles of this invention.

After the wet granules are dried, the solidified binder preferably dissolves quickly upon contact with water. The type and quantity of binder in solutions for wet granulation can be adjusted to make the granules with desirable physical properties, such as high plasticity and good binding properties. Other pharmaceutically acceptable organic solvents, such as ethanol, can also be used as a solvent for the binder, which may further decrease the dissolution of the porous materials. Other materials include carbohydrates listed in Component 2, and polymers such as acacia, alginic acid, CARBOMER, carboxymethylcellulose, cellulose, dextrin, ethylcellulose, gelatin, hydroxyethylcellulose, hydroxypropylcellulose, hydroxypropyl methylcellulose, methylcellulose, polydextrose, poly(ethylene oxide), povidone, and sodium alginate.

Other Components

In addition to the above mentioned three components, some other components can also be added to the tablet formulation to improve the tablet quality and performance. Disintegrant, sweeteners, flavors, coloring agents, souring agents, and lubricant can be added. Exemplary disintegrants include starches, crosslinked polyvinylpyrrolidone, croscarmellose sodium, sodium starch glycolate, and superporous hydrogel. Sweeteners include natural and artificial sweeteners, such as sodium saccharin, aspartame, and cyclamate. Examples of flavor agents include fruit flavor, bubble gum flavor, and the like. The coloring agents include food dyes, food lake dye, and the like. Souring agents, which induce salivation in the use, include citric acid. The lubricants include sodium stearate, stearic acid, poly(ethylene glycol), polyoxypropylene-polyoxyethylene block polymers, talc, sodium stearyl fumarate, colloidal silicon dioxide, and the like.

Process of Making Fast Melting Tablets Based on Highly Plastic Granules

Addition of Active Components: Active pharmaceutical ingredients, e.g., drugs, can be added to the formulation by several methods. A drug, or drugs, can be mixed with Component 1 and Component 2, as shown in FIG. 1, and then undergo wet granulation. A drug, or drugs, can also be added to Component 3 for granulation, as shown in FIG. 2. Alternatively, a drug, or drugs, can be mixed with placebo highly plastic granules, as depicted in FIG. 3. The placebo highly plastic granules are those prepared in the absence of a drug or drugs. Other points of introduction of the drug into the formulation, which may depend upon the stability properties of the drug, are within the skill of the trained practitioner. As used herein, "dietary supplements" are considered within the definition of "active pharmaceutical ingredients".

The active pharmaceutical ingredient can be in crystalline, amorphous, or any solid form. Drug particles can be coated to mask taste or control the drug release profile. Surfactants, superdisintegrants, superporous hydrogel particles, effervescent agents, lubricants, flavoring agents, or coloring agents can be optionally added to improve tablet performances and/or manufacturing processes.

Granulation for making highly plastic granules: Depending on the state of granulation, the method of granulation can be changed. In wet granulation, other desired materials, in addition to drug, Component 1, Component 2, and other necessary components, can be added. After all components are mixed, a solution for wet granulation is added gradually while the dry materials are continuously stirred until a wet mass with desirable properties is obtained. Low shear granulators, high shear granulators or fluid bed granulators are preferred for wet granulation to avoid excessive damage to the inner porous structure of primary particles. In the granulation process, highly plastic granules of Component 1 and Component 2 can be made separately and then mixed later. During the wet granulation process, particles are forced to come close together and liquid bridges are formed in between particles. This is why the wet granulation method is said to be a densification process. The resultant wet mass is screened through a sieve with a desired sieve size and dried.

The material choices of components are such that the obtained granules become highly plastic even after drying. The highly plastic granules can be used for making tablets by compression. The exact steps for wet granulation can be varied depending on the equipment used for wet granulation. The main point here is to make highly plastic granules.

During wet granulation, dry components may partially be dissolved in solution, and thus they may lose the porosity of their primary particles to some extent. To minimize this from happening, a solution for wet granulation with a high binder concentration is used to decrease the dissolution power of the solution for diluents and dry binders. Another advantage of using solutions for wet granulation of high binder concentrations is that the amount of binder deposited on the particles will be very high, leading to significant improvement in binding between particles during compression. The term "high binder concentration" refers to concentrations higher than those used in conventional granulations, and preferably concentrations close to the saturated solution concentration of a binder. The binder for granulation is not limited to the solution state, and semi-solids can be added as a binder in granulation.

Sieving and Drying: In the sieving step, the wet mass passes though a sieve before drying. The drying method or condition can be varied to achieve the highly plastic property of the final dry granules. The wet granulation, sieving, and drying step can be combined depending on the granulation equipment.

Pre-Compression: The granules may be mixed with superdisintegrant, superporous hydrogel particles, effervescent agents, lubricants, flavoring agents, or coloring agents in a blender before compression at low pressures (1-150 MPa).

Compression: For a tablet to melt fast in the mouth, it has to absorb water quickly into its inner core. Thus, maintaining high porosity in the compressed tablet is important. Usually, low pressure is applied to maintain high porosity after compression. When tablets are made at low compression pressure, however, they usually show poor friability and hardness. A major difference between tablets prepared according to the present invention and other so-called "fast dissolving" tablets is that the tablets of this invention have high plasticity. When a force or stress is applied to granules, the stress force is released in two different ways. If the granules return to their original shape or form, it is called elastic deformation. If the granules do not totally recover their shapes after the stress is released, it is called plastic deformation. While both elastic and plastic deformations can occur simultaneously, only one effect usually dominates during the compression process [Dor, P., et al., *Pharma. Devel. & Tech.*, 5: 575-577, 2000]. As the applied force increases, the thickness of the tablet decreases. In the meantime, when granules are compressed, granules go through particle rearrangement, elastic deformation, plastic deformation, and brittle fracture. Tablets gain significant strength only at the plastic deformation and fracture stage. In the present approach, the force necessary to reach the plastic deformation stage dramatically decreases due to the use of highly plastic granules. Because this stage comes early, significant porosity can be maintained while gaining significant tablet strength. Because of the high plasticity of the granules, very low friability can be achieved at an early stage of compression (i.e., at the low pressure region) when porosity between particles is not significantly reduced. Combined with inner porosity of the porous and plastic materials and water penetration enhancer, the tablet can maintain very high porosity. Both high strength and low friability can be achieved at low compression pressure.

In summary, fast-melting tablets can be prepared at low compression pressure using highly plastic granules that comprise three components used in granulation. A high binder concentration is important for depositing high amounts of binder to the surface of particles. Conventional wet granulation methods can be used based on the three-component system to make highly plastic granules that are ideal for making fast melting tablets at low compression pressure.

Active Pharmaceutical Ingredients

The present invention can be employed with a wide range of active pharmaceutical ingredients, far too numerous to mention individually here. For example, representative classes of drugs that can be formulated into the fast melting tablets of the present invention include:

Anti-migraine drugs such as almotriptan, ergotamine tartrate, frovatriptan, methysergide maleate, sumatriptan succinate, zolmitriptan, and the like;

Anti-rheumatic drugs such as auranofin, azathioprine, cyclosporine, hydroxychloroquine sulfate, lefumomide, methotrexate, penicillamine, sulfasalazine, and the like;

Non-steroidal anti-inflammatory drugs such as acetaminophen, aspirin, dichlorofenac, etodolac, fenoprofen, ibuprofen, ketoprofen, naproxen, indomethacin, ketololac, sulindac, tolmetin, mechlofanamate, mefenamic acid, nabumetone, meloxicam, piroxicam, celecoxib, rofecoxib, and the like;

Opioids such as buprenorphine, codeine, fentanyl, hydrocodone, hydromorphone, lavorphanol, meperidine, morphine, oxycodone, pentazocine, propoxyphene, tramadol, and the like;

Anti-mycobacterial drugs such as aminosalicylic acid salts, clofazimine, cycloserine, ethionamide, rifabutin, and the like;

Anti-parasite drugs such as albendazole, ivermecin, mebendazole, praziquantel, and the like;

Anti-viral drugs such as valacyclovir, didanosine, famciclovir, valganciclovir, indinavir, lamivudine, nelfinavir mesylate, nevirapine, ritonavir, stavudine, oseltamivir phosphate, and the like;

Beta-lactams such as amoxicillin, amoxicillin and potassium clavulanate, ampicillin, cefuroxime sodium, cefuroxime axetil, penicillin G and V salts, cefditoren, cefixime, cloxacillin sodium, dicloxacillin sodium, and the like;

Macrolide antibiotics such as erythromycin estolate, erythromycin ethylsuccinate, erythromycin stearate, and the like;

Fluoroquinolones such as ciprofloxacin, enoxacin, and the like;

Tetracyclines such as demeclocycline hydrochloride, doxycycline calcium, tetracycline, tetracycline hydrochloride, and the like;

Alkylating agents such as altretamine, busulfan, chlorambucil, melphalan, cyclophosphamide, procarbazine hydrochloride, temozolomide, and the like;

Antimetabolites such as methotrexate, mercaptopurine, thioguanine, and the like;

Hormonal drugs and antagonists such as bicalutamide, flutamide, nilutamide, aminoglutethimide, anastrozole, exemestane, letrozole, tamoxifen citrate, toremifene citrate, and the like;

Mitotic inhibitors such as etoposide phosphate, and the like;

Immunosuppressants such as azathioprine, cyclosporine, mycophenolate mofetil, sirolimus, tacrolimus, and the like;

Antiarrhythmic drugs such as amiodarone hydrochloride, digoxin, disopyramide phosphate, dofetilide, flecainide acetate, mexiletine hydrochloride, moricizine hydrochloride, procainamide hydrochloride, propafenone hydrochloride, quinidine sulfate, quinidine gluconate, sotalol hydrochloride, tocainide, and the like;

Antihypertensive drugs such as doxazosin mesylate, prazosin hydrochloride, terazosin hydrochloride, benazepril, captopril, clonidine hydrochloride, enalapril, hydrolazine hydrochloride, labetalol hydrochloride, losartan potassium, methyldopate hydrochloride, minoxidil, moexipril, trandolapril, candesartan, irbesartan, losartan, telmisartan, valsartan, guanabenz acetate, guanadrel sulfate, guanfacine hydrochloride, reserpine, and the like;

Beta-adrenergic blocking drugs such as acebutolol, atenolol, betaxolol, bisoprolol, carteolol, carvedilol, labetalol, metoprolol, nadolol, penbutolol, pindolol, propranolol, soltalol, timolol, and the like;

Calcium-channel blocking agents such as amlodipine, bepridil, diltiazem, felodipine, isradipine, nicardipine, nifedipine, nimodipine, nisoldipine, verapamil, and the like;

Hypolipidemic drugs such as fenofibrate, gemfibrozil, niacin, atorvastatin, fluvastatin, lovastatin, pravastatin, simvastatin, and the like;

Nitrates such as isosorbide dinitrate, nitroglycerin, nitroprusside sodium, and the like;

Anticonvulsants such as carbamazepine, clonazepam, ethosuximide, felbamate, gabapentin, lamotrigine, levetiracetam, oxcarbazepine, phenobarbital, phenytoin, primidone, tiagabine, topiramate, valproic acid, divalproex sodium, zonisamide, and the like;

Antidepressants such as mirtazapine, bupropion, amoxapine, phenelzine, tranylcypromine, citalopram, fluoxetine, fluvoxamine, paroxetine, sertraline, venlafaxine, maprotiline, trazodone, nefazodone, amitriptyline, clomipramine, desipramine, dexepin, imipramine, nortriptyline, protryptyline, trimipramine, and the like;

Antipsychotic drugs such as chlorpromazine, thioridazine, loxapine, molindone, clozapine, olanzapine, quetiapine, risperidone, ziprasidone, fluphenazine, haloperidol, perphenazine, trifluoperazine, thiothixene, and the like;

Anxiolytics, sedatives, and hypnotics such as alprazolam, lorazepam, oxazepam, chlordiazepoxide, clorazepate, diazepam, halazepam, midazolam, triazolam, zaleplon, zolpidem, estazolam, temazepam, flurazepam, quazepam, meprobamate, phenobarbital, chloral hydrate, ethchlorvynol, glutethimide, pentobarbital, secobarbital, and the like;

Neurodegenerative disease drugs such as amantadine, benztropine mesylate, carbidopa and levodopa, donepezil, bromocriptine, pergolide, pramipexole, ropinirole, and the like;

Ophthalmic drugs for glaucoma such as acetazolamide, dichlorphenamide, methazolamide, and the like;

Drugs for acid-peptic therapy such as aluminum carbonate, aluminum hydroxide, magnesium hydroxide, sodium bicarbonate, calcium carbonate, magaldrate, and the like;

Bismuth salts, cimetidine, famotidine, nizatidine, ranitidine, misoprostol, lansoprazole, omeprazole, pantoprazole, rabeprazole, sucralfate, and the like;

Antiemetics such as buclizine, cyclizine, dimenhydrinate, diphenhydramine, meclizine, dronabinol, chlorpromazine, perphenazine, prochlorperazine, promethazine, thiethylperazine, triflupromazine, dolasetron, granisetron, ondansetron, dexamethasone, larazepam, and the like;

Gastrointestinal motility drugs such as bisacodyl, diphenoxylate hydrochloride and atropine sulfate, docusate salts, loperamide, magnesium salts, metoclopramide, ussodiol, and the like;

Coagulants and anticoagulants such as clopidogrel bisulfate, phytonadione, ticlopidine, warfarin sodium, and the like;

Hematopoietics such as ferrous salts, and the like;

Adrenal hormones such as cortisone, hydrocortisone, methylprednisolone, prednisone, triamcinolone, betamethasone, dexamethasone, fludrocortisone, and the like;

Antidiabetic drugs such as acarbose, metformin, nateglinide, repaglinide, acetohexamide, chlorpropamide, tolazamide, tolbutamide, glimepiride, glipizide, gluburide, pioglitazone, rosiglitazone, and the like;

Contraceptives such as norethindrone, norgestrel, levonorgestrel, and the like;

Female sex hormones such as estradiol and its esters, estrogens, estropipate, medroxyprogesterone, mifepristone, norethindrone acetate, progesterone, raloxifene, and the like;

Thyroid and antithyroid drugs such as iodides, levothyroxine sodium, liothyronine sodium, liotrix, methimazole, propylthiouracil, and the like;

Diuretics such as amiloride hydrochloride, bumetanide, ethacrynic acid, furosemide, torsemide, hydrochlorothiazide, chlorthiazide, chlorthalidone, indapamide, metolazone, polythiazide, quinethazone, trichlormethiazide, spironolactone, triamterene, and the like;

Electrolytes such as chelated magnesium, magnesium chloride, magnesium hydroxide, magnesium oxide, potassium salts, and the like;

Gout therapy drugs such as allopurinol, colchicine, probenecid, sulfinpyrazone, and the like;

Antiasthmatics such as albuterol sulfate, montelukast sodium, theophylline, zileuton, and the like;

Antihistamines such as acrivastine, azatadine, bromopheniramine maleate, carbinoxamine maleate, cetirizine hydrochloride, chlorpheniramine maleate, diphenhydramine hydrochloride, clemastine fumarate, cyproheptadine hydrochloride, fexofenadine, hydroxyzine, loratadine, desloratadine, and the like;

Cough and cold drugs such as dextromethorphan hydrobromide, guaifensin, pseudoephedrine hydrochloride, and the like; and Nutritional supplements.

Characterization of Fast Melting Tablets

Tablet strength: Tablet strength was measured by a texture analyzer (TA XT2®, Texture Technologies Corp.; Scarsdale, N.Y.). The force that causes a diametrical failure (i.e., clear breaking) of a tablet was taken as the indicator for the tablet strength.

Disintegration test: This method is a modified version of the method developed by Dor et al., supra. The method utilized a texture analyzer (TA XT2®). A tablet was adhered to the bottom of a probe, which is attached to the load cell, with a very thin layer of glue or a double-sided copper tape. With constant force, the tablet was approached to a filter paper soaked with water, which was connected to a water reservoir. When the tablet started to disintegrate, the rate of movement that the probe travels showed a sudden increase. This increased rate continued until the tablet was disintegrated. The time that the increased rate of movement was stopped was taken as the disintegration time.

In vivo disintegration tests of FDTs were conducted on volunteers. Volunteers were usually randomized to receive the treatments and then directed to clean their mouths with water. Tablets were placed on their tongues, and the time for disintegration was measured by immediately starting a stopwatch. The volunteers were allowed to move FDTs against the upper roof of the mouth with their tongue and to cause a gentle tumbling action on the tablet without biting on it or tumbling it from side to side. Immediately after the last noticeable granule was disintegrated, the stopwatch was stopped and the time recorded.

Friability test: The tablet friability test method was performed according to the USP 25 tablet friability method described in <1216> Tablet Friability of the General chapters describing General Tests and Assays.

The present invention is now described in terms of certain examples solely for purposes of illustration and explanation, and not by way of limitation.

EXAMPLES

Example 1

| Ingredients: | |
|---|---|
| Maltrin QD580 | 6 g |
| Mannogem EZ spray | 24 g |

Maltrin (Component 1) is maltodextrins and corn syrup solids in quick-dispersing forms sold by Grain Processing Corp. (Muscatine, Iowa) and Mannogem EZ spray (Component 2) is spray-dried mannitol from SPI Pharma. Inc. (New Castle, Del.). Maltrin QD580 of size between No. 20 and No. 60 sieves was used. Maltrin QD580 and Mannogem EZ spray were mixed together. Then the bulk mixture was geometrically mixed with a small mixture to get the full mix. 7 ml of 70% sucrose binding solution (Component 3) was added to the mixture while mixing with a mixer. The mixture went through a No. 18 sieve and air dried at room temperature. The dried mixture went through a No. 30 sieve. The granules were then compressed into tablets at 300 lb in a ½ inch die by a Caver press. The weight of each tablet was 500 mg. The hardness of the tablet was 65.2 N and disintegration time was 23 seconds.

Example 2

| Ingredients: | |
|---|---|
| Maltrin 180 | 6 g |
| Mannogem EZ spray | 24 g |

Maltrin 180 and Mannogem EZ spray were mixed together. Then the bulk mixture was geometrically mixed with a small mixture to get the full mix. 6 ml of 70% sucrose binding solution was added to the mixture while mixing with a mixer. The mixture went through No. 18 sieve and air dried at room temperature. The dried mixture went through a No. 30 sieve. The granules were then compressed into tablets at 300 lb in a ½ inch die by a Caver press. The weight of each tablet was 500 mg. The hardness of the tablet was 7.3 N. Maltrin 180 has exactly the same molecular structure as Maltrin QD580. The only difference is the bulk density. Maltrin 180 is a nonporous version with the packed bulk density of 0.61 g/cc while Maltrin QD580 is a porous version with the packed bulk density of 0.40 g/cc. Because the Maltrin 180 is nonporous, much less plastic deformation would occur when Maltrin 180 is compressed as compared with Maltrin QD580 compressed at the same condition. When the granules are compressed at low pressure, the higher plastic deformation results in higher possibility of forming bonding between granules. The major difference between Examples 1 and 2 is use of Maltrin 180 in Example 2 instead of Maltrin QD580 in Example 1. The tablet strength is significantly increased when Maltrin QD580 was used.

Example 3

Maltrin QD580 of size between No. 20 and No. 60 sieves was used and the Mannogem EZ spray went through a No. 50 sieve. The two materials were mixed in proportions as listed in the table below. The granules were then compressed into tablets at 300 lb in a ½ inch die by a Caver press. The weight of each tablet was 500 mg. The hardness of the prepared tablets is shown in Table 1. Without granulation by adding a binder, the direct compression of those two materials did not yield tablets with desirable strength as compared with tablets in Example 1. Tablets made of pure Maltrin QD580 had higher strength than tablets with pure Mannogem EZ spray presumably because of more plastic deformation during compression by Maltrin QD580. Adding a binder to porous and plastic materials leads to good bonding among particles for making tablets with high mechanical strength.

TABLE 1

| Percentage of material in the mixture | | |
|---|---|---|
| Mannogem EZ spray (%) | Maltrin QD580 (%) | Hardness (N) |
| 100 | 0 | 5.2 |
| 90 | 10 | 5.4 |
| 80 | 20 | 4.2 |
| 70 | 30 | 4 |
| 50 | 50 | 6.1 |
| 20 | 80 | 8.4 |
| 0 | 100 | 9.1 |

Example 4

Maltrin QD580 of size between No. 20 and No. 60 sieves was used. Mannogem EZ spray particles were passed through a No. 50 sieve. 100 g of Maltrin QD580 and 400 g of Mannogem EZ spray were mixed. The mixture was put into a Kitchen-Aid mixer. The speed was kept at 1 when dry mixing. The dry mixing took 5 min. 100 ml of sucrose solution ranging from 10% to 70% sucrose solution was pumped into the mixer by a Gilson mini Puls2 peristaltic pump at a rate of 40 ml/min. After all the binder solution was introduced, the mixer was continued to run for 2 min. The wet mass was passed through a No. 8 sieve. The granules were then compressed into tablets at 300 lb in a ½ inch die by a Caver press. The weight of each tablet was 500 mg. The results are shown in Table 2 below.

TABLE 2

| Sucrose concentration (%) | Hardness (N) | Disintegration (seconds) |
|---|---|---|
| 10 | 3.6 | 4.98 |
| 30 | 10.8 | 15.9 |
| 50 | 20.1 | 14.3 |
| 70 | 36.5 | 14.2 |

The results indicate that as the concentration of the sucrose concentration increases, the hardness increases substantially due to more plastic deformation inducing better bonding. This is most likely due to the preservation of porous structures by using binder solutions with high sucrose concentrations.

Example 5

| Ingredients: | |
|---|---|
| Maltrin QD500 | 6 g |
| StarLac | 12 g |
| Mannogem EZ spray | 12 g |

StarLac (Component 1) is spray-dried solid containing 15% maize starch and 85% alpha-lactose monohydrate from Roquette American, Inc. (Keokuk, Iowa). To a mixture of the above three materials is gradually added 6 ml of 70% sorbitol solution (Component 3). The obtained wet mass was passed through a No. 18 sieve, and the wet granules were placed in a 50° C. oven for 22 hours. The granules were removed from the oven and left in air at room temperature for 2 hours, and then passed through a No. 30 sieve. Granules of 200 mg were poured into a 0.375 inch die and subsequently compressed at 150 lb. When the formed tablets were placed in the mouth, they melt in less than 10 seconds, usually within 6 seconds. When the friability test was performed according to the US Pharmacopoeia, the friability was only 1.3%.

Example 6

| Ingredients: | |
|---|---|
| Maltrin QD580 | 6 g |
| StarLac | 12 g |
| Mannogem EZ spray | 12 g |

The process was the same as shown in Example 5. 200 mg tablets were obtained. The disintegration time was measured to be 8 seconds for these tablets.

Example 7

| Ingredients: | |
|---|---|
| Maltrin QD580 | 6 g |
| StarLac | 12 g |
| Silicified microcrystalline cellulose | 12 g |
| Loratadine | 1.8 g |

The silicified microcrystalline cellulose (Component 2) used is PROSOLV SMCC 90 by Penwest Company (Patterson, N.Y.). To a mixture of the above four ingredients was gradually added 6 ml of 70% sorbitol solution, preferably adding 0.2 ml aliquots of the sorbitol solution while mixing with a hand mixer. The obtained wet mass was passed through a No. 18 sieve, and the wet granules were placed in a 50° C. oven for 22 hours. The granules are removed from the oven and left in air at room temperature for 2 hours, and then passed through a No. 30 sieve. Granules were poured into a 0.375 inch die and subsequently compressed at 150 lb. The weight of each tablet was 200 mg. The average disintegration time was 13 seconds.

Example 8

| Ingredients: | |
|---|---|
| Maltrin QD580 | 6 g |
| Mannogem EZ spray | 24 g |
| Aspirin | 17.8 g |
| Zinc gluconate | 0.98 g |
| Glucosamine sulfate | 4.95 g |

Maltrin QD580 of size between No. 20 and No. 60 sieves was used. Maltrin QD580, Mannogem, aspirin, zinc gluconate and glucosamine sulfate were mixed together. 8 ml 70% Sucrose binding solution were added to the mixture while mixing with a hand mixer. The mixture went through a No. 18 sieve and air dried at room temperature. The dried mixture was passed through a No. 30 sieve. For each 100 g of the granules, 3 g of POLYPLASDONE® XL (Crospovidone by International Specialty Products corp., Calvert Cit, Ky.) and 1.7 g aspartame were added. The resultant mixture was compressed into tablets at 300 lb in a 7/16 inch die by a Caver press. The weight of each tablet was 314 mg. The average disintegration time was 14.3 seconds and friability was 0.45%. The hardness of the tablet was 54.9 N.

Example 9

| Ingredients: | |
|---|---|
| Maltrin QD580 | 200 g |
| Mannogem EZ spray | 767 g |
| Loratadine | 33 g |

Maltrin QD580 was passed through a No. 30 sieve, and Mannogem EZ spray through a No. 50 sieve. The mixture of the above three ingredients were poured into a 6 liter high shear mixer container. Diasona mixer granulator P1-6 was used for mixing at impeller speed of 200 rpm and chopper speed of 1,500 rpm. All ingredients were premixed for 1 min, and then 160 ml of a 50% sucrose in 50% ethanol solution was pumped at a rate of 400 ml/min. The wet mass was mixed for 2 more minutes. After stopping the binding solution, the wet mass was sieved through a No. 8 sieve and air dried. The dried granules were sieved through a No. 16 sieve. For every 100 g of granules, 3 gram of POLYPLASDONE® XL was added and mixed. The resultant mixture was compressed into tablets at 300 lb in a 7/16 inch die by a Caver press. The weight of each tablet was 309 mg, the average disintegration time was 9 seconds, and the hardness of the tablet was 20.6 N.

Example 10

| Ingredients: | |
|---|---|
| Maltrin QD580 | 89.4 g |
| Mannogem EZ spray | 357.6 g |
| Folic acid | 33.0 g |
| Vitamin B12 | 0.5 g |

Maltrin QD580 was sieved through a No. 30 sieve, and the Mannogem EZ spray through a No. 50 sieve. The above four ingredients were mixed and the mixture was then poured into a 6 liter high shear mixer container. Diasona mixer granulator P1-6 was used for mixing at impeller speed of 200 rpm and chopper speed of 1500 rpm. All ingredients were premixed for 1 min. Then 100 ml of the 50% sucrose in 50% ethanol solution was pumped in at a rate of 200 ml/min. The wet mass was mixed for 2 more minutes. After stopping the flow of the binding solution, the wet mass was sieved through a No. 8 sieve and air dried. The dried granules were passed through a No. 16 sieve. For every 100 gram of granules, 3 gram of POLYPLASDONE® XL was added and mixed. The resultant mixture was compressed into tablets at 200 lb in a ⅜ inch die by a Caver press. The weight of each tablet was 309 mg. The average disintegration time was 6 seconds. The hardness of the tablet was 18.4 N.

Example 11

| Ingredients: | |
| --- | --- |
| Maltrin QD580 | 6 g |
| Mannogem EZ spray | 24 g |
| Acetaminophen | 30 g |

Maltrin QD580 of size between No. 20 and No. 60 sieves was used. Maltrin QD580, Mannogem, acetaminophen were mixed together. 8 ml of 70% sucrose binding solution was added to the mixture while mixing with a hand mixer. The mixture was passed through a No. 18 sieve and air dried in the room. The dried mixture was sieved using a No. 30 sieve. For every 100 gram of granules, 3 gram of POLYPLASDONE® XL was added and mixed. The resultant mixture was compressed into tablets at 300 lb in a 9/16 inch die by a Caver press. The weight of each tablet was 309 mg. The average disintegration time was 25 seconds, and the hardness of the tablet was 49.2 N.

Example 12

| Ingredients: | |
| --- | --- |
| Maltrin QD580 | 5 g |
| Calcium Carbonate | 25 g |

Maltrin QD580 of size between No. 20 and No. 60 sieves was used. Maltrin QD580 and calcium carbonate (Component 2) were mixed. 6 ml of 70% sucrose binding solution was added to the mixture while mixing with a hand mixer. The mixture was passed through a No. 18 sieve and air dried in the room. The dried mixture was passed through a No. 30 sieve. The resultant mixture was compressed into tablets at 500 lb in a 9/16 inch die by a Caver press. The weight of each tablet was 1,000 mg. The average disintegration time was 25 seconds and the hardness of the tablet was 24.5 N.

Example 13

| Ingredients: | |
| --- | --- |
| Maltrin QD580 | 6 g |
| Mannogem EZ spray | 24 g |
| Herbal Extract | 3.5 ml (aqueous solution) |

Maltrin QD580 was passed through a No. 30 sieve, and the Mannogem EZ spray through a No. 50 sieve. Aqueous solution (2.5 ml) herbal extract was added to the sucrose solution to make a final sucrose concentration of 70%. 8 ml of 70% sucrose binding solution containing herbal extract was added to the mixture while mixing with a hand mixer. The mixture was passed through a No. 18 sieve and air dried in the room. The dried mixture was sieved using a No. 20 sieve. For every 100 gram of granules, 3 gram of POLYPLASDONE® XL was added and mixed. The resultant mixture was compressed into tablets at 250 lb in a 5/16 inch die by a Caver press. The weight of each tablet was 150 mg. The average disintegration time was 7 seconds, and the hardness of the tablet was 25 N.

Example 14

| Ingredients: | |
| --- | --- |
| Maltrin QD580 | 6 g |
| Mannogem EZ spray | 24 g |

Maltrin QD580 was passed through a No. 30 sieve, and the Mannogem EZ spray through a No. 50 sieve. 8 ml of 85% sucrose binding solution was added to the mixture while mixing with a hand mixer. The mixture was passed through a No. 18 sieve and air dried in the room. The dried mixture was sieved using a No. 18 sieve. To the highly plastic granules was mixed sodium bicarbonate at the ratio of 2:1 (highly plastic granule:sodium bicarbonate) along with 2% lubricant. The final mixture was compressed into tablets at 200 lb in a ¼ inch die by a Caver press. The weight of each tablet was 60 mg. The average disintegration time was 7 seconds.

Example 15

| Ingredients: | |
| --- | --- |
| Maltrin QD580 | 200 g |
| Mannogem EZ spray | 800 g |

Maltrin QD580 was passed through a No. 30 sieve, and the Mannogem EZ spray through a No. 50 sieve. The mixture of the above two ingredients was poured into a 6 liter high shear mixer container. Diasona mixer granulator P1-6 was used for mixing at the impeller speed of 200 rpm and the chopper speed of 1500 rpm. All ingredients were premixed for 1 min, and then 240 ml of 50% sucrose in 50% ethanol solution was pumped into the mixture at a rate of 400 ml/min. The wet mass was mixed for 2 more minutes. After stopping the binding solution, the wet mass was sieved through a No. 8 sieve and air dried. The dried granules went through a No. 16 sieve. Two grams of mint oil and 98 g of the placebo granules were mixed together. The resultant mixture was compressed into tablets at 250 lb in a 7/16 inch die by a Caver press. The weight of each tablet was 300 mg. The average disintegration time was 6.6 seconds, and the hardness of the tablet was 16.5 N.

Example 16

| Ingredients: | |
|---|---|
| Advantose FS 95 Fructose (SPI Pharma) | 31.21 g |
| Mannogem EZ spray | 93.63 g |

Advantose FS 95 Fructose is a co-dried material of 95% fructose and 5% starch. Advantose FS 95 Fructose and Mannogem EZ spray were mixed together and 25.2 g of 50% sucrose solution were added while mixing with a hand mixer. The obtained wet mass was passed through a No. 25 sieve, and then air dried. The dried granules were passed through a No. 30 sieve. Obtained granules were mixed with additional materials for compression, as indicated in Table 3.

TABLE 3

| Ingredients | Composition |
|---|---|
| Granules | 137.44 g |
| Magnesium stearate | 1.47 g |
| Stearic acid | 1.47 g |
| Crospovidone | 7.39 g |
| Total | 147.77 g |

The resultant mixture was compressed into tablets in a ⅜ inch die by a single punch tablet machine (EK-0, Korsch, Germany). The weight of each tablet was 200 mg. The average disintegration time was 26 seconds, and the hardness of the tablet was 22 N. When the friability test was performed according to the US Pharmacopoeia, the friability was 1.12%.

Example 17

| Ingredients: | |
|---|---|
| Loratadine | 29.96 g |
| Mannogem EZ spray | 352.05 g |
| Advantose FS 95 Fructose (SPI Pharma) | 117.35 g |

Loratadine, Advantose FS 95 Fructose and Mannogem EZ spray were mixed together and 99.87 g of 50% sucrose solution was added while mixing with a hand mixer. The obtained wet mass was passed through a No. 25 sieve, and then air dried. The dried granules were passed through a No. 30 sieve. Obtained granules were mixed with additional materials for compression as indicated in Table 4.

TABLE 4

| Ingredients | Composition |
|---|---|
| Granules | 549.29 g |
| Magnesium stearate | 5.97 g |
| Stearic acid | 5.97 g |
| Crospovidone | 29.85 g |
| Aspartame | 0.6 g |
| Cherry Flavor | 2.98 g |
| Total | 594.66 g |

The resultant mixture was compressed into tablets in a ⅜ inch die by a single punch tablet machine (EK-0, Korsch, Germany). The weight of each tablet was 200 mg. The average disintegration time was 30 seconds, and the hardness of the tablet was 26 N. When the friability test was performed according to the US Pharmacopoeia, the friability was 1.23%.

Example 18

| Ingredients: | |
|---|---|
| Loratadine | 7.29 g |
| Mannogem EZ spray | 117.56 g |

Loratadine and Mannogem EZ spray were mixed together and 48.0 g of 50% sucrose solution were added while mixing with a hand mixer. The obtained wet mass was passed through a No. 25 sieve, and then air dried. The dried granules were passed through a No. 30 sieve. Obtained granules were mixed with additional materials for compression as shown in Table 5. (This example illustrates the use of Mannogem EZ as both Component 1 and Component 2, because it is also porous in addition to enhancing water penetration, although more binder solution is required and the properties of surface, mouthfeel, hardness and friability may be compromised.)

TABLE 5

| Ingredients | Composition |
|---|---|
| Granules | 148.85 g |
| Magnesium stearate | 1.60 g |
| Stearic acid | 1.60 g |
| Crospovidone | 8.00 g |
| Total | 160.05 g |

The resultant mixture was compressed into tablets in a ⅜ inch die by a single punch tablet machine (EK-0, Korsch, Germany). The weight of each tablet was 200 mg. The average disintegration time was 35 seconds, and the hardness of the tablet was 23 N. When the friability test was performed according to the US Pharmacopoeia, the friability was 1.84%.

Example 19

| Ingredients: | |
|---|---|
| Advantose 100 Maltose (SPI Pharma) | 31.21 g |
| Mannogem EZ spray | 93.63 g |

Advantose 100 Maltose (Component 1) is spray dried disaccharide carbohydrate. Advantose 100 Maltose and Mannogem EZ spray were mixed together and 28.16 g of 50% sucrose solution were added while mixing with a hand mixer. The obtained wet mass was passed through a No. 25 sieve, and then air dried. The dried granules were passed through a No. 30 sieve. Obtained granules were mixed with additional materials for compression as indicated in Table 6.

TABLE 6

| Ingredients | Composition |
| --- | --- |
| Granules | 138.92 g |
| Magnesium stearate | 1.49 g |
| Stearic acid | 1.49 g |
| Crospovidone | 7.47 g |
| Total | 149.37 g |

The resultant mixture was compressed into tablets in a ⅜ inch die by a single punch tablet machine (EK-0, Korsch, Germany). The weight of each tablet was 200 mg. The average disintegration time was 38 seconds, and the hardness of the tablet was 18.5 N. When the friability test was performed according to the US Pharmacopoeia, the friability was 1.73%.

The present invention has been described above with reference to certain examples for purposes of explanation and clarification. It should be appreciated that various improvements and modifications of the invention can practiced within the scope of the appended claims.

What is claimed is:

1. A method of making a fast-melting pharmaceutical tablet, comprising:
   combining a plastic substance, and a water penetration enhancer to form an admixture thereof;
   treating the admixture with an aqueous binder solution effective to form a mass of agglomerated particles thereof, wherein the binder solution contains 70% to 85% sucrose;
   sieving and/or drying the agglomerated particles so as to isolate a plurality of highly plastic granules; and
   compressing the highly plastic granules with a tablet press under a compression pressure less than about 150 MPa to afford the fast melting pharmaceutical tablet, which melts in the mouth in less than about 60 seconds.

2. The method of claim 1, further comprising intimately combining an active pharmaceutical ingredient with the plastic substance, the water penetration enhancer, and/or the binder prior to admixing the plastic substance and the water penetration enhancer.

3. The method of claim 1, wherein the plastic substance is water soluble or water dispersible.

4. The method of claim 1, wherein the plastic substance is a powder having a porous structure that exhibits plastic deformation whenever 500 mg of the powder is compressed into a 0.5-inch diameter die at a pressure less than about 1,500 pounds.

5. The method of claim 1, wherein the water penetration enhancer is characterized by exhibiting complete wetting of a 200 mg tablet comprised thereof within 60 seconds after contacting a 0.5 ml water drop provided on a flat surface on which the water drop does not spread, which tablet is formed at 300 pounds in a 0.5 inch diameter die.

6. The method of claim 1, wherein the binder is dissolved in aqueous solution or a mixture of water and an organic solvent prior to said treating.

7. The method of claim 1, wherein the compression pressure is less than about 35 MPa.

8. The method of claim 7, wherein the compression pressure is less than about 10 MPa.

9. The method of claim 1, further comprising combining the highly plastic granules with at least one additional ingredient prior to compressing.

10. The method of claim 9, wherein the at least one additional ingredient is selected from the group consisting of surfactants, superdisintegrants, superporous hydrogel particles, effervescent agents, lubricants, flavoring agents, and coloring agents.

11. The method of claim 1, wherein the plastic substance and the water penetration enhancer are identical substances.

12. The method of claim 1, wherein the agglomerated particles are subjected to mixing with a high shear mixer, low shear mixer, or fluid bed mixer.

13. The method of claim 1, wherein the drying entails air drying, vacuum drying, oven drying, fluidized bed drying, or microwave drying.

14. A pharmaceutical tablet having fast dissolving properties made by the method of claim 1.

15. The method of claim 1, further comprising intimately combining an active pharmaceutical ingredient with the highly plastic granules prior to compressing.

16. A pharmaceutical tablet having fast dissolving properties made by the method of claim 15.

* * * * *